Oct. 23, 1962 D. L. ARMSTRONG ET AL Plant Pat. 2,187
ROSE PLANT
Filed Nov. 7, 1961
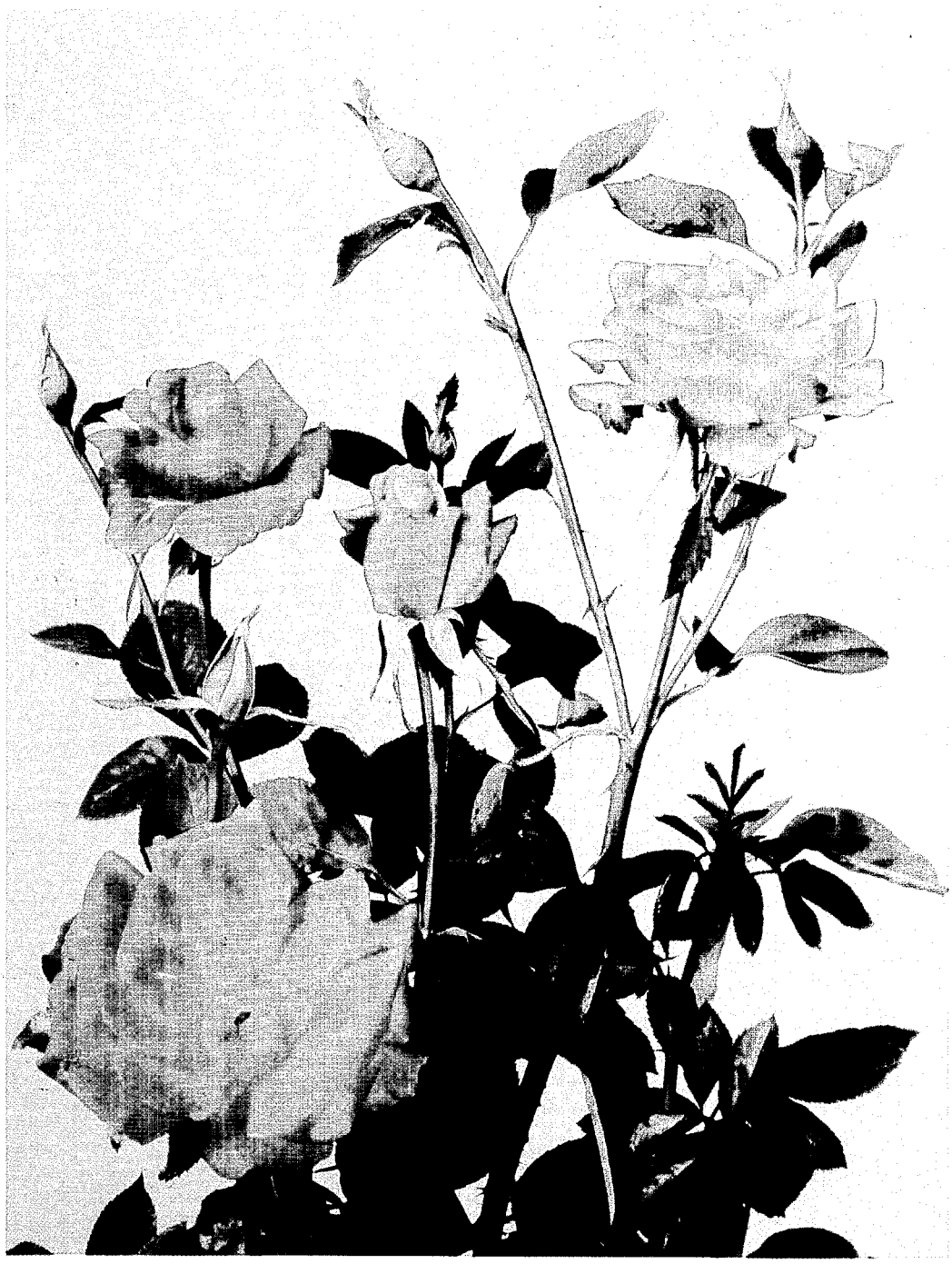
Inventors.
David L. Armstrong
Herbert C. Swim
By: Robb & Robb
Attorneys.

United States Patent Office

Plant Pat. 2,187
Patented Oct. 23, 1962

2,187
ROSE PLANT

David L. Armstrong and Herbert C. Swim, Ontario, Calif., assignors to Armstrong Nurseries, Inc., Ontario, Calif., a corporation of California Filed Nov. 7, 1961, Ser. No. 150,842
1 Claim. (Cl. 47—61)

The present invention relates to a new and distinct variety of rose plant of the hybrid tea class, which was originated by us by crossing the variety "Charlotte Armstrong" (Plant Patent No. 455) with the variety "Montezuma" (Plant Patent No. 1383), the former being the seed parent, and the latter being the pollen parent.

The general objective of this breeding was to produce a new and improved rose variety of the hybrid tea type, in which the flower color falls in the pink, orange-red, and pure red color range, combined with the excellent bud and flower form of the parent variety "Charlotte Armstrong" and the excellent form of the bud and half-open flower corresponding to that of the parent variety "Montezuma." An additional objective was to obtain in the new variety improved vigor and floriferousness corresponding to that of the parent variety "Montezuma." These objectives, together with other desirable improvements, were fully achieved, as evidenced by the following unique combination of characteristics which distinguish the new variety from its parents, as well as from all other varieties of which we are aware:

(1) A vigorous, upright-spreading, moderately open habit of plant growth;

(2) Attractive dark green leaves of from medium to large size, with the new growth being of reddish color;

(3) Greater than average floriferousness in comparison with other hybrid tea rose varieties;

(4) Relatively large flowers of medium petalage, with the flowers usually borne on single stems, but sometimes in small clusters;

(5) Good urn-shaped buds of moderate length, with the half-open and open flowers having a very attractive high-centered form and petal arrangement similar to that of the parent variety "Charlotte Armstrong";

(6) Excellent petal substance, with attendant long-lasting flowers; and (7) Distinctive and attractive bright red flowers which are relatively non-bluing and non-fading, with the general color tonality ranging between Cherry and Rose Red.

In comparison with its seed parent, "Charlotte Armstrong," the new variety is somewhat more spreading in its habit of growth, and the flower color is darker, brighter, more rich and non-bluing, with the color ranging between Cherry and Rose Red, as distinguished from the light red or dark pink and more bluish cerise color of the flowers of "Charlotte Armstrong."

In comparison with its pollen parent, "Montezuma," the flowers of the new variety are borne more often on single stems of somewhat greater length than those of the variety "Montezuma," and the flower color, ranging between Cherry and Rose Red, is a bright, rich and darker red than the more Salmon Red or Salmon Pink color of the flowers of "Montezuma."

Asexual reproduction of our new variety by budding, as performed at Ontario, California, shows that the foregoing characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated as "Wilson") and Robert Ridgway's Color Standards and Nomenclature (hereinafter abbreviated as "Ridgway"), as indicated:

Type: Bush; outdoor; seedling; for cut flowers and for garden decoration.

Class: Hybrid tea.

Breeding: Seedling.

*Seed parent.*—"Charlotte Armstrong."

*Pollen parent.*—"Montezuma."

Propagation: Holds its distinguishing characteristics through succeeding propagations by budding.

*Flower*

Locality where grown and observed: Ontario, California.

Flowers borne: Usually singly, but sometimes from 3 to 5 to stem; in irregular cluster; on stems of normal strength and from medium to long length.

Quantity of bloom: Abundant, outdoors.

Continuity: Nearly continuous during growing season.

Fragrance: From slight to moderate.

Bud:

*Peduncle.*—Average length; from average caliper to heavy; erect; usually smooth, sometimes with few small stipitate glands and few hairs. Color—near Absinthe Green, Plate XXXI (Ridgway), overlaid with near Yellowish Olive, Plate XXX (Ridgway) on side exposed to sun.

*Before calyx breaks.*—Size—medium. Form—medium length; ovoid.

*As calyx breaks.*—Color—near Chrysanthemum Crimson, Plate 824, page 169 (Wilson), with areas exposed longer to sun near Purple Madder, Plate 1028, page 181 (Wilson).

*Sepals.*—Inner surface—with fine, wooly tomentum. Outer surface—usually with from few to several small stipitate glands. Alternate margins—lined with fine, wooly tomentum. Other margins—with from few to several small stipitate glands and foliaceous parts of medium size, and with foliaceous appendages usually extending from ¼ to ½ or more of the length of the bud beyond the tip.

*As first petal opens.*—Size—from average to large. Form—from medium length to long; ovoid; usually becoming urn-shaped. Color: outside—between Currant Red, Plate 821/3, page 167 (Wilson) and Cardinal Red, Plate 822/2, page 168 (Wilson), with small area at base of petal near attachment near Sulphur Yellow, Plate 1/1, page 1 (Wilson); inside—near Cardinal Red, Plate 822, page 168 (Wilson), blending with near Cardinal Red, Plate 822/3, page 168 (Wilson) toward base of petal, with small area at base near attachment near Sulphur Yellow, Plate 1, page 1 (Wilson).

*Opening.*—Opens up well; is not retarded or prevented from opening by cold, hot, wet or dry weather.

Bloom:

*Size (when fully open).*—From average to large; from 3½ inches to 4½ inches.

*Petalage.*—Double; from 26 to 30 petals, plus 4 to 12 petaloids; arranged irregularly.

*Form.*—High-centered at first but becoming cupped to high-centered; petals being at first tightly cupped, with tips reflexed outward, but later becoming more loosely flat to cupped, with tips reflexed outward, at maturity; outer and intermediate petals of newly opened flower usually reflexed outward both along edges of petals and at apex; outer and intermediate petals of three-days open flower usually reflexed strongly outward both along edges of petals and at apex.

Petals:

*Texture.*—Medium thickness. Inside—slightly velvety. Outside—satiny.

*Shape.*—Outside—broadly obovate, with apex flat, and sometimes with from 1 to 3 notches. Intermediate—obovate, with apex rounded, and sometimes with from 1 to 3 notches. Inside—narrowly obovate, with apex rounded.

This description of a newly opened flower was made from a rose grown outdoors during the month of September at Ontario, California:

*Color.*—Outer petal: outside surface—between Rose Red, Plate 724, page 158 (Wilson) and Cardinal Red, Plate 822/3, page 168 (Wilson), with small area at base of petal near attachment near Sulphur Yellow, Plate 1, page 1 (Wilson); inside surface—near Cardinal Red, Plate 822/1, page 168 (Wilson), blending with near Cardinal Red, Plate 822/3, page 168 (Wilson) toward base of petal, with small area at base near Sulphur Yellow, Plate 1, page 1 (Wilson). Intermediate petal: outside surface—between Crimson, Plate 22/1, page 22 (Wilson) and Rose Madder, Plate 23, page 23 (Wilson), with small area at base near attachment near Sulphur Yellow, Plate 1, page 1 (Wilson); inside surface—near Rose Red, Plate 724, page 158 (Wilson), blending with near Cherry, Plate 722/3, page 158 (Wilson) toward base of petal, with small area at base near Sulphur Yellow, Plate 1, page 1 (Wilson). Inner petal: outside surface—between Crimson, Plate 22, page 22 (Wilson) and Rose Madder, Plate 23, page 23 (Wilson) with small area at base of petal near attachment near Sulphur Yellow, Plate 1, page 1 (Wilson); inside surface—near Rose Red, Plate 724, page 158 (Wilson), blending with near Cherry, Plate 722, page 157 (Wilson), with small area at base of petal near attachment near Sulphur Yellow, Plate 1, page 1 (Wilson).

This description was made from a rose that was open for 3 days outdoors during the month of September at Ontario, California:

*Color.*—Outer petal: outside surface—between Rose Madder, Plate 23/1, page 23 (Wilson) and Tyrian Rose, Plate 24/1, page 24 (Wilson) with small area at base near attachment near Primrose Yellow, Plate 601/2, page 65 (Wilson); inside surface—near Rose Red, Plate 724, page 158 (Wilson), blending with near Rose Madder, Plate 23/1, page 23 (Wilson) toward base of petal, with small area near attachment near Primrose Yellow, Plate 601/3, page 65 (Wilson). Inner petal: outside surface—between Rose Madder, Plate 23/1, page 23 (Wilson) and Tyrian Rose, Plate 24/2, page 24 (Wilson), with small area at base of petal near attachment near Primrose Yellow, Plate 601/2, page 65 (Wilson); inside surface—near Rose Red, Plate 724, page 158 (Wilson), blending with near Rose Madder, Plate 23/2, page 23 (Wilson) toward base of petal, with small area near attachment near Primrose Yellow, Plate 601/2, page 65 (Wilson); sometimes petals of both newly opened and 3-days open flower have vegetative streak extending from base toward apex of petal with color of streak near Sap Green, Plate 62/3, page 62 (Wilson).

*General color effect.*—Newly opened flower—between Cherry, Plate 722/2, page 157 (Wilson) and Rose Red, Plate 724, page 158 (Wilson). 3-days open—near Rose Red, Plate 724, page 158 (Wilson).

*Behavior.*—Drop off cleanly; not particularly affected by cold, hot, wet or dry weather.

*Flower longevity.*—On bush in garden—4 or 5 days in September. Cut roses grown outdoors and kept at living-room temperatures—5 or 6 days in September.

*Reproductive Organs*

Stamens: Average number; arranged regularly about pistils; a few mixed with petaloids.

Filaments: From short to medium length (from 5 to 12 mm.); most with anthers. Color—near Empire Yellow, Plate 603/1, page 66 (Wilson).

Anthers: From small to medium size; all open approximately at once. Color: upper side—margins near Apricot, Plate 609, page 70 (Wilson), with remainder near Straw Yellow, Plate 604/2, page 67 (Wilson); under side—margins near Apricot, Plate 609, page 70 (Wilson), with remainder near Straw Yellow, Plate 604/2, page 67 (Wilson).

Pollen: Moderately abundant. Color—near Cadmium Orange, Plate 8, page 8 (Wilson).

Pistils: Average number (approximately 70).

Styles: Moderately even; from short to average length (from 4 to 10 mm.); thin caliper; bunched. Color—upper ⅓ near Crimson, Plate 22/1, page 22 (Wilson), with remainder near Primrose Yellow, Plate 601/2, page 65 (Wilson).

Stigma: Color—near Maize Yellow, Plate 607/2, page 69 (Wilson).

Ovaries: Usually all enclosed in calyx.

Hips: Average length; from flat to globular; with inconspicuous neck; smooth; walls thick and fleshy. Color (⅔ mature)—near Absinthe Green, Plate XXXI (Ridgway).

Sepals: Usually falling soon.

Seeds: Average number (usually from 8 to 12 per hip from open pollinated flowers); medium size.

*Plant*

Foliage:

*Leaves.*—Compound of usually 3–7 leaflets; from normal quantity to abundant; from medium size to large; leathery; semi-glossy.

*Leaflets.*—Shape—oval, with apex acute. Base—between round and acute. Margin—doubly serrate.

*Color.*—Mature: upper surface—between Forest Green, Plate XVII (Ridgway) and Empire Green, Plate XXXII (Ridgway); under surface—near Asphodel Green, Plate XLI (Ridgway). Young: upper surface—near Dark Corinthian Purple, Plate XXXVIII (Ridgway); under surface—near Mineral Red, Plate XXVII (Ridgway).

*Rachis (the supporting stem of the compound leaf).*—From light to average size. Upper side—grooved; with from few to several stipitate glands on edges. Under side—smooth; with from none to few stipitate glands and from none to few prickles.

*Stipules.*—Short; narrow; with short points turning out at an angle of less than 45°.

*Disease resistance.*—Better than average resistance to mildew, as compared with other varieties grown under comparable cultural conditions at Ontario, California.

Growth:

*Habit.*—Upright-spreading; moderately branched.

*Growth.*—Vigorous.

*Canes.*—Heavy.

*Main stems.*—Color—near Biscay Green, Plate XVII (Ridgway). Large prickles—from several to many; moderately short; hooked slightly downward; with narrow base of medium length; color—near Army Brown, Plate XL (Ridgway). Small prickles—from several to many; color—near Army Brown, Plate XL (Ridgway). Hairs—none.

*Branches.*—Color—near Light Elm Green, Plate XVII (Ridgway). Large prickles—from few to several; medium length; hooked downward; with long, narrow base; color—near Fawn color, Plate XL (Ridgway). Small prickles—from several to many; color—near Fawn color, Plate XL (Ridgway). Hairs—none.

*New shoots.*—Color—near Dull Citrine, Plate XVI (Ridgway), overlaid with near Sorghum Brown, Plate XXXIX (Ridgway) on side exposed to the sun. Large prickles—from several to many; medium length; hooked downward; with long, narrow base. color—near Hydrangea Red, Plate XXVII (Ridgway). Small prickles—from none to few; Color—near Hydrangea Red, Plate XXVII (Ridgway). Hairs—none.

We claim:

A new and distinct variety of rose plant of the hybrid tea class, substantially as herein shown and described, characterized particularly as to novelty by the unique combination of a vigorous, upright-spreading, and moderately open habit of plant growth, attractive dark green leaves of from medium to large size, with the new growth being of reddish color, greater than average floriferousness, relatively large flowers of medium petalage borne usually on single stems but sometimes in small clusters, good urn-shaped buds of moderate length, the flowers in the half-open and open stages having an attractive high-centered form and petal arrangement similar to the flowers of "Charlotte Armstrong" (Plant Patent No. 455), excellent petal substance with attendant long-lasting flower qualities, and a distinctive and attractive bright red general color tonality of the flowers, said color being relatively non-bluing and non-fading and ranging between Cherry and Rose Red.

No references cited.